(12) United States Patent
Cesa et al.

(10) Patent No.: US 7,491,838 B2
(45) Date of Patent: Feb. 17, 2009

(54) PURIFICATION OF ACETONITRILE BY A DISTILLATIVE RECOVERY/ION EXCHANGE RESIN TREATMENT PROCESS

(75) Inventors: Mark Clark Cesa, South Euclid, OH (US); Paul Alan Jacobson, Victoria, TX (US); Richard Lee Wappelhorst, Port Lavaca, TX (US)

(73) Assignee: INEOS USA LLC, Lisle, IL (US)

( * ) Notice: Subject to any disclaimer, the term of this patent is extended or adjusted under 35 U.S.C. 154(b) by 286 days.

(21) Appl. No.: 10/648,572

(22) Filed: Aug. 26, 2003

(65) Prior Publication Data

US 2004/0176631 A1 Sep. 9, 2004

Related U.S. Application Data

(63) Continuation of application No. 08/632,382, filed on Apr. 10, 1996, now abandoned.

(51) Int. Cl.
*C07C 253/34* (2006.01)

(52) U.S. Cl. ..................................................... 558/463
(58) Field of Classification Search .................. 558/463
See application file for complete search history.

(56) References Cited

U.S. PATENT DOCUMENTS 3,313,726 A * 4/1967 Campbell et al. ............. 521/26
4,362,603 A * 12/1982 Presson et al. ................ 203/75

FOREIGN PATENT DOCUMENTS

GD DD 259 530 A3 * 8/1988

* cited by examiner

*Primary Examiner*—James O. Wilson
*Assistant Examiner*—Ebenezer Sackey
(74) *Attorney, Agent, or Firm*—David P. Yusko

(57) ABSTRACT

A process of producing HPLC grade acetonitrile (UV cut-off<190) comprising a multistep distillation under reflux conditions followed by acidic ion exchange resin treatment to remove essentially all impurities from the acetonitrile.

17 Claims, 1 Drawing Sheet

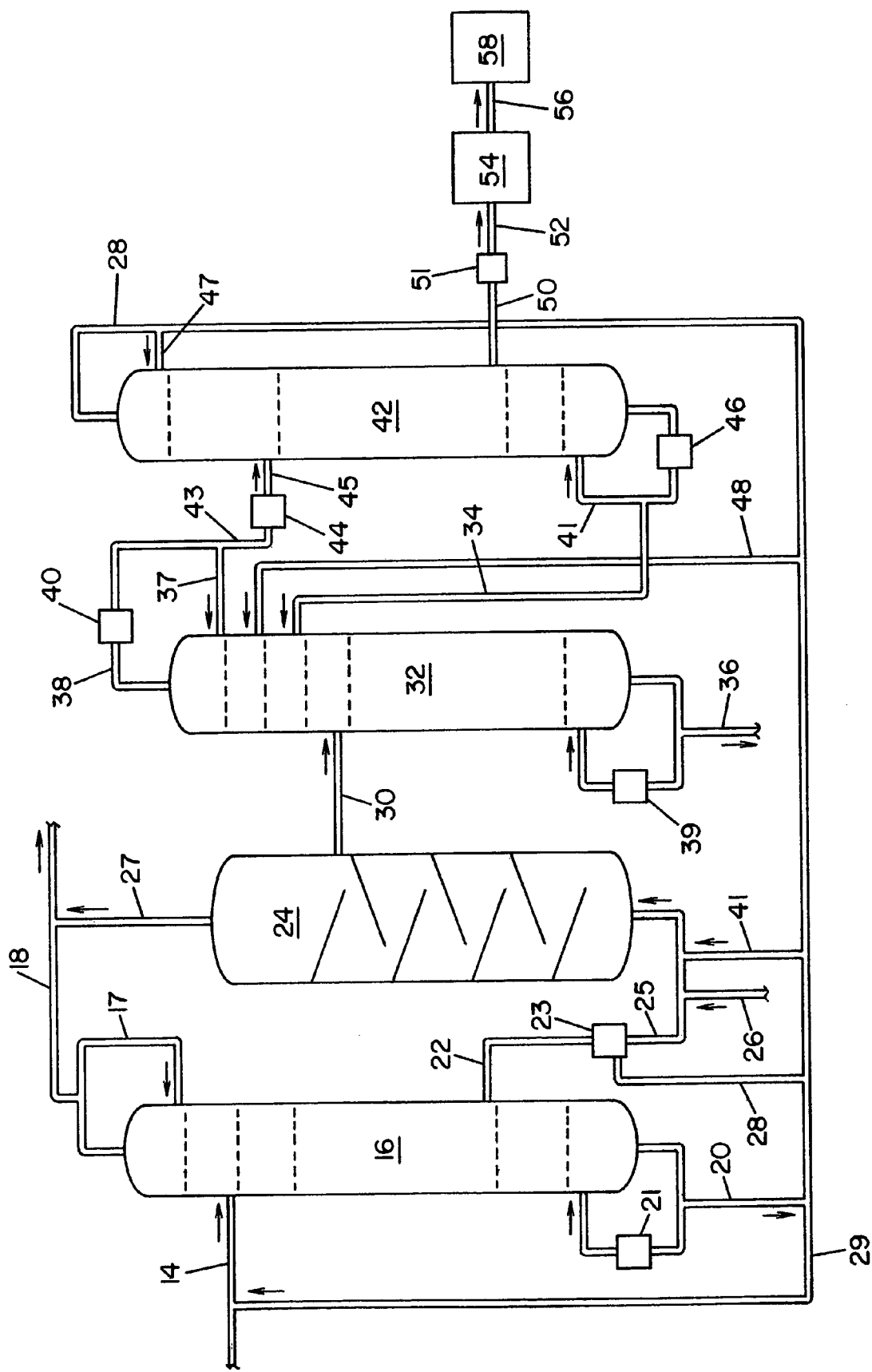

US 7,491,838 B2

PURIFICATION OF ACETONITRILE BY A DISTILLATIVE RECOVERY/ION EXCHANGE RESIN TREATMENT PROCESS

REFERENCE TO RELATED APPLICATIONS

This is a continuation of U.S. patent application Ser. No. 08/632,382 filed Apr. 10, 1996, now abandoned.

BACKGROUND OF THE INVENTION

Field of the Invention

In the production of acrylonitrile by the catalytic ammoxidation of propylene with ammonia and oxygen, a crude acetonitrile co-product is produced. The term "crude acetonitrile" means liquid acetonitrile containing hydrogen cyanide, water and other impurities. The other impurities may include acrylonitrile, acetaldehyde, acetone, methanol, acrolein, oxazole, cis- and trans-crotononitrile, methacrylonitrile and allyl alcohol. The relative proportions of the components of the crude acetonitrile can vary over a wide range depending on various conditions. The concentration level of the organic impurities in the crude acetonitrile is usually less than 15% with no single organic component found in greater than 2 to 4 wt % concentration. Usually crude acetonitrile obtained from an acrylonitrile plant contains between 25 and 85% acetonitrile. Typically, the crude acetonitrile is composed on a weight basis of 52% acetonitrile, 43.6% water, 2.5% hydrogen cyanide, 0.5% acrylonitrile and 1.3% other organic impurities as mentioned above. Originally, during the manufacture of acrylonitrile, the crude acetonitrile produced was disposed of by incineration. However, in recent years, this material has been recovered and purified and sold to add value to the process.

There are two basic technologies for the "first stage" purification of crude acetonitrile co-product produced during the manufacture of acrylonitrile. These processes typically produce acetonitrile of sufficient purity for use as a bulk solvent. The first and most common practiced technology is a batch process. In this process, crude acetonitrile is distilled to remove the bulk of the HCN as a low boiling distillate. Then the remaining material is allowed to react either with a mixture of strong base, usually sodium hydroxide and formaldehyde and water, or with a strong base and ferrous sulfate, to remove essentially all the remaining HCN. (See U.S. Pat. Nos. 4,328,075 and 3,201,451.) The HCN free material is then distilled to produce an acetonitrile/water azeotrope containing about 25% water, which in turn is then slurried with anhydrous calcium chloride to remove the bulk of the water in the azeotrope and produce an acetonitrile/water mixture containing about 3 to 5% water. This mixture is then distilled to produce acetonitrile product having an acceptable purity for many uses. Typically, this material contains several parts per million by weight of acrylonitrile or other impurities which absorb strongly in the UV spectrum.

The second method of producing "first stage" purified acetonitrile is a continuous recovery process which involves first distilling crude acetonitrile in a distillation zone at a pressure of at or above 1 atmosphere to remove the bulk of the HCN, passing this azeotrope through a digester in which the remaining HCN is removed by treatment with an aqueous solution of base and formaldehyde, performing a second distillation at a pressure less than 1 atmosphere to separate the material into a bottoms product containing water and a second acetonitrile/water azeotrope with higher acetonitrile concentration, and (4) a third distillation at a pressure above the pressure of the first distillation to produce purified acetonitrile as a side stream. This process is described in U.S. Pat. No. 4,362,603 assigned to the assignee of the present invention and herein incorporated by reference. Acetonitrile purified by this method can contain up to several hundred parts per million by weight of acrylonitrile, acetamide, oxazole, or other UV-absorbing impurities.

While these two basic procedures for forming bulk solvent grade acetonitrile are widely accepted, their use in producing acetonitrile for chromatographic applications is not acceptable because they contain a relatively high amount of UV-absorbing impurities. There is a distinct market for high performance (HPLC grade) acetonitrile essentially free of UV-absorbing impurities (UV cutoff for impurities of <190 nm).

The specifications for HPLC grade acetonitrile render the material produced by first stage purification unacceptable, therefore requiring further processing by producers of HPLC grade acetonitrile. The traditional commercial methods of acetonitrile purification to achieve this high grade of purity utilize costly multi-step processes involving, for example, permanganate oxidation, acid treatment, phosphorous pentoxide drying and two distillations.

More recent procedures disclosed in U.S. Pat. Nos. 5,292,919 and 5,426,208 disclose treatment of acetonitrile with ozone followed by passing the acetonitrile through a series of adsorbent beds of charcoal or graphitized carbon, activated alumina, and/or molecular sieves.

Several other patents and literature articles describe the purification of acetonitrile with acidic ion exchange resins for removal of impurities from acetonitrile. British Patent 1,223,915 describes the use of a series of strong acid cation exchange resins for the reduction of the concentration of bases, ammonia and 3,3'-iminodipropionitrile, in aqueous acetonitrile from 500 ppm each to 10 ppm and <50 ppm, respectively. This level of purity is still not acceptable for HPLC grade acetonitrile.

The process of the present invention is directed to a procedure for producing HPLC grade acetonitrile without the attendant disadvantages of numerous steps and high cost.

SUMMARY OF THE INVENTION

It is an primary object of the present invention to produce HPLC grade acetonitrile.

It is a secondary object of the present invention to produce HPLC grade acetonitrile from crude acetonitrile obtained as a coproduct during the manufacture of acrylonitrile.

Additional objects, advantages and novel features of the invention will be set forth in part in the description which follows, and in part will become apparent to those skilled in the art upon examination of the following or may be learned by the practice of the invention. The objects and advantages of the invention may be realized and obtained by means of the instrumentalities and combinations particularly pointed out in the appended claims.

To achieve the foregoing objects in accordance with the purpose of the present invention as embodied and described therein, the method of the present invention comprises (1) distilling crude acetonitrile in a first distillation column affixed with a first overhead reflux loop at a first pressure of at least 1 atmosphere to remove HCN, producing a first acetonitrile/water azeotrope and a first bottom product containing water, (2) distilling the first azeotrope in a second distillation column affixed with a second overhead reflux loop at a second pressure less than 1 atmosphere to separate the first azeotrope into a second bottoms product containing water and a second acetonitrile/water azeotrope having a greater acetonitrile concentration than the first azeotrope, (3) distilling the second acetonitrile/water azeotrope in a third distillation column affixed with a third overhead reflux loop at a third pressure above 1 atmosphere to produce a third acetonitrile/water azeotrope containing substantially all of the water from the second azeotrope, a third bottoms product comprising acetonitrile and heavy organics, and a side stream comprising highly pure acetonitrile, and (4) passing the highly pure acetonitrile side stream through an acidic ion exchange resin to further purify said highly pure acetonitrile producing HPLC grade acetonitrile wherein the reflux ratios in Steps 1, 2 and 3 are kept at greater than 3 to 1, greater than 3.4 to 1 and greater than 6.4 to 1, respectively.

The term "reflux ratio" as used above is defined as follows: for the first column (light ends column), the reflux ratio is defined as the ratio of overhead reflux flow rate divided by the rate of feed from the column side to the digester. For the second distillation (drying column), the reflux ratio is defined as the ratio of overhead reflux flow rate to the rate of the overhead draw-off to the product column. For the third distillation column (product column), the reflux ratio is defined as the ratio of overhead reflux flow rate to the rate of acetonitrile product side stream flow.

In a preferred embodiment of the present invention the light ends column reflux ratio is preferably greater than 4.4 to 1, the drying column reflux ratio is preferably greater than 4.5 to 1 and the product column reflux ratio is preferably greater than 8 to 1. Especially preferred is a light ends column reflux ratio of greater than 5.2 to 1, a drying column reflux ratio of greater than 5 to 1 and a product column reflux ratio of greater than 10.9 to 1.

The acidic ion exchange resins are used in their $H^+$ form. Regeneration of resin beds can be carried out by passing sulfuric acid or hydrochloric acid solutions over the resin beds by any conventional procedure known to the art. After regeneration, the resin bed is washed with several bed volumes of acetonitrile to dry the bed and remove impurities.

The resin treatment step can be carried out in any mode known in the art. The resin treatment step can be carried out preferably as a continuous fixed bed process, although slurry mode operation in (optionally) stirred tank reactors, for example, is within the scope of this invention. The adsorbent beds can be operated in a continuous mode at ambient temperature or at elevated or reduced temperature as required, and with either upward or downward flow, with temperatures from 15 to 35° C. being preferred. A flow rate ranging from about 0.1 to 300 bed volumes per hour is within the scope of the process of the present invention, although operating outside this range is also satisfactory. Preferably, flow rates are in the range of 0.2 to 50 bed volumes per hour. Most preferably, from 0.5 to 35 bed volumes per hour.

Lastly, a final distillation of the HPLC grade acetonitrile is optional and may be carried out by conventional means known in the art. Preferably, means of distillation are distillation in glass or stainless steel equipment, although other materials of construction inert to acetonitrile and free of contaminants are within the scope of the invention. Fractionation can be accomplished with Oldershaw columns, or columns packed with beds, helices, trays, turnings, saddles, or other conventional packing material known in the art.

Suitable ion exchange resins useful in the practice of the present invention include strong acid type incorporating sulfonic acid functional groups, either gel form or macroreticular or macroporous form. Examples include, but are not restricted to, Amberlyst 15, Amberlyst XN 1010, Dowex 50, Amberlite IRP-69, Amberlite IR-118, and their equivalents. Also acceptable but less preferred are the so-called weak acid resins incorporating carboxylic acid functional groups, either gel form or macroreticular or macroporous form. Examples of this class of resin include, but are not restricted to, Amberlite IRP-64 and IRC-50S. Particularly preferred are the strong acid resins specifically designed for non-aqueous applications, such as Amberlyst 15.

BRIEF DESCRIPTION OF THE DRAWING

The FIGURE is a flow diagram of the practice of the process of the present invention.

DETAILED DESCRIPTION OF THE INVENTION

In accordance with the present invention, crude acetonitrile is processed to recover highly pure acetonitrile as a valuable byproduct. By "highly pure" acetonitrile is meant High Performance Liquid Chromatography (HPLC) grade acetonitrile, acetonitrile of extremely high purity and being sufficiently free of UV absorbing impurities (well below 0.1 to 0.3 ppm max) having a UV absorbance cut off of <190 nm. The crude acetonitrile which is processed in accordance with the present invention is any acetonitrile/water mixture containing at least 15% water. Thus, the inventive process is applicable in the processing of various water/acetonitrile azeotropes. The invention, however, finds broadest application in the processing of the crude acetonitrile streams produced by the ammoxidation of propylene with oxygen and ammonia to form acrylonitrile. As indicated above, such crude acetonitrile streams normally contain about 52% acetonitrile, 43.6% water, 0.5% acrylonitrile, 2.5% HCN and 1.3% other minor impurities such as oxazole, allyl alcohol, acetone and propionitrile.

Crude acetonitrile recovered from an acrylonitrile plant and having the above composition can be conveniently processed by the present invention in accordance with the flow scheme illustrated in the FIGURE. In accordance with this system, the crude acetonitrile is fed via inlet line 14 into light ends column 16 wherein it is distilled at a temperature of between about 140° F. to 160° F. (preferably 144° F. to 155° F., especially preferred being 148° F. to 152° F.) at a pressure of about 18 psia to three phases. The light components in the crude acetonitrile, namely HCN, acrylonitrile, oxazole and acetone, are withdrawn from light ends column 16 as a vapor draw and are condensed and refluxed back into the upper region of column 16 via reflux line 17. Preferably, the reflux ratio as defined above is greater than 3:1. Unrecovered overheads are removed via line 18 and transported to vent scrubbers (not shown) for waste treatment. Water is recovered from the bottom of light ends column 16 and discharged via line 20 to waste treatment with partial recycle through reboiler 21. A first acetonitrile/water azeotrope containing about 70% acetonitrile, 30% water, 500 ppm HCN and very small amounts of heavy organics is recovered via line 22 as a vapor side draw condensed in condenser 23 and transported via line 25 to digester 24.

An HCN digester composition comprising an aqueous solution of sodium hydroxide and formaldehyde is added via line 26 to digester 24 so that the HCN and acrylonitrile in the first azeotrope is destroyed.

The HCN-free acetonitrile/heavy organics and water mixture passing out of digester 24 is charged via line 30 into drying column 32 and unrecovered material is removed from digester 24 as overheads via line 27 and combined in line 18 for transport to vent scrubber and waste treatment. In addition, a stream comprising acetonitrile containing a small amount of heavy impurities is also charged into drying column 32 via line 34 from product column 42. In drying column 32, the acetonitrile/heavy organics and water mixture is distilled at a pressure below one atmosphere, e.g. 3.4 psi and heavy organics are discharged for waste treatment via line 36 with some recycled back via reboiler 39 into the bottom of column 32, and a gaseous top draw comprising a second acetonitrile/water azeotrope, the second azeotrope containing about 10% water, is removed from column 32 via line 38. At least part of this second azeotrope is condensed and refluxed back into column 32 via reflux line 37. The reflux ratio in this step as defined above is greater than 3.4:1.

The second acetonitrile/water azeotrope is charged via line 38 into condenser 40 where it is condensed, passed via line 43 through heat exchanger 44 where it is heated, and then charged via line 45 into product column 42. In product column 42, the second acetonitrile/water azeotrope is distilled at high pressure, e.g. 50 psia, into three phases. A bottoms product comprising acetonitrile containing heavy impurities is withdrawn from the bottom of product column 42 into reboiler 46 for partial recycling to column 42 via line 41 and drying column 32 via line 34. A third acetonitrile/water azeotrope is withdrawn from the top of product column 42 via line 28 condensed and recycled as reflux back to the top of product column 42 via reflux line 47. The uncondensed vapors continue via line 28 to the azeotrope condenser 23 where they are mixed with the first azeotrope. Alternatively, these uncondensed vapors may be rerouted to light ends column 16 via lines 29 and 14. Preferably, the reflux ratio as defined above of greater than 6.4:1 for this step of the process. In an alternative embodiment of the present invention, some liquid from product column overhead stream 28 may be recycled to drying column 32 via line 48 or digester 24 via line 41. Because product column 42 is operated at high pressure, all of the water in the second acetonitrile/water azeotrope charged into product column 42 is recovered in the overhead stream of product column 42, i.e. the third acetonitrile/water azeotrope, leaving high purity acetonitrile in the product column. This high purity acetonitrile (99.8 wt % acetonitrile) is drawn off column 42 as a sidestream via line 50 (This stream may be a vapor or liquid, preferably a vapor), and after cooling in heat exchanger 51 is discharged via line 52 into resin treatment bed 54 where it is treated to produce HPLC grade acetonitrile which is recovered via line 56 in product tank 58.

The temperature for distillation in drying column 32 fluctuates between about 75° F. to 90° F., preferably between 78° F. to 88° F. The typical distillation temperature in the product column is between about 250° F. to 260° F., preferably 255° F. to 258° F.

The following Examples set forth below are illustrative of the practice of the present invention.

EXAMPLE 1

Acetonitrile was recovered from crude acetonitrile in a continuous recovery unit at light ends column reflux ratio 3:1, drying column reflux ratio 6.8:1, and product column reflux ratio>12:1. The recovered acetonitrile contained 3.3 mg/L oxazole, 10.3 mg/L acetamide, and 0.01 wt % water. Allyl alcohol, acrylonitrile, cis- and trans-crotononitrile, methacrylonitrile, and pyridine were below detection limits. The UV spectrum of this material showed absorbances of 0.0020 at 254 nm, 0.0767 at 220 nm, and 1.1462 at 190 nm. A resin bed was prepared from 9.69 g of fresh, dry Amberlyst 15 ion exchange resin, H+ form, bed diameter 1.2 cm, bed length 20 cm. After the bed was flushed with 240 mL of acetonitrile at 80 mL/hr, a 440 mL sample of acetonitrile was passed through the resin by downward flow at 80 mL/hr at room temperature. The UV spectrum of the eluent in a 1 cm path length cell showed absorbances of 0.0060 at 254 nm, 0.0182 at 220 nm, and 0.4775 at 190 nm. This compares favorably with the ACS specifications for UV absorbance for HPLC grade acetonitrile of 0.01 max at 254 nm, 0.05 max at 220 nm, and 1.0 max at 190 nm. An HPLC gradient analysis was run on this sample, using a Phenomenex column, IB-SIL, 5 µm, 250×4.6 mm, with 100% acetonitrile for 10 minutes, then 80% water/20% acetonitrile for 50 minutes, then again 100% acetonitrile for 10 minutes. The chromatogram showed no peaks above 2 mAU absorbance at 254 nm, comparing favorably with the ACS specification of no peaks above 5 mAU absorbance.

EXAMPLE 2

Acetonitrile was recovered from crude acetonitrile in a continuous recovery unit at light ends column reflux ratio approximately 6.7:1, drying column reflux ratio approximately 4.0:1, and product column reflux ratio approximately 11:1. The recovered acetonitrile contained 1.8 mg/L oxazole, 7.9 mg/L acetamide, and 0.01 wt % water. Allyl alcohol, acrylonitrile, cis- and trans-crotononitrile, methacrylonitrile, and pyridine were below detection limits. The UV spectrum of this material in a 1 cm path length cell showed absorbances of 0.0006 at 254 nm, 0.0707 at 220 nm, and 0.9970 at 190 nm. A resin bed was prepared from 10.1 g (20 cc)of fresh, dry Amberlyst 15 ion exchange resin, H+ form, bed diameter 1.2 cm, bed length 20 cm. After the bed was flushed with 200 mL of acetonitrile at 80 mL/hr, 1480 mL of acetonitrile was passed through the resin by downward flow at 80 mL/hr at room temperature. The UV absorbance of the combined eluent in a 1 cm path length cell after filtration through a 0.2µ Nylon filter disk at 254 nm was 0.0031, at 220 nm 0.0143, and at 190 nm 0.4791. This compares favorably with the ACS specifications for UV absorbance for HPLC grade acetonitrile of 0.01 max at 254 nm, 0.05 max at 220 nm, and 1.0 max at 190 nm, and also compares favorably with a sample of commercial HPLC grade acetonitrile, whose UV spectra in a 1 cm path length cell showed absorbances of 0.0030 at 254 nm, 0.0141 at 220 nm, and 0.4766 at 190 nm. An HPLC gradient analysis was run on this sample, using a Phenomenex column, IB-SIL, 5 µm, 250×4.6 mm, with 100% acetonitrile for 10 minutes, then 80% water/20% acetonitrile for 50 minutes, then again 100% acetonitrile for 10 minutes. The chromatogram showed no peaks above 4 mAU absorbance at 254 nm, comparing favorably with the ACS specification of no peaks above 5 mAU absorbance.

500 g of the Amberlyst 15-treated material was then placed in a 1 L three neck flask affixed with a 30 cm×1 cm i.d. glass vacuum jacketed fractionating column, unpacked, and a coldfinger distillation head. The ground glass joints were sealed with Teflon tape. The first 16.7 g of distillate was discarded, and the remaining distillate was collected together and filtered through a 0.2µ Nylon filter disk. 3.4 g of pot residue remained. The UV spectrum of the collected distillate in a 1 cm path length cell showed absorbances of 0.0000 at 254 nm, 0.0083 at 220 nm, and 0.4430 at 190 nm, superior to the absorbances of the commercial HPLC grade acetonitrile. An HPLC gradient analysis was run on this sample, using a Phenomenex column, IB-SIL, 5 µm, 250×4.6 mm, with 100% acetonitrile for 10 minutes, then 80% water/20% acetonitrile for 50 minutes, then again 100% acetonitrile for 10 minutes. The chromatogram showed no peaks above 3 mAU absorbance at 254 nm, comparing favorably with the ACS specification of no peaks above 5 mAU absorbance.

COMPARATIVE EXAMPLE 1

Acetonitrile was recovered from crude acetonitrile in a batch recovery unit and contained 17.4 mg/L oxazole, 3.4 mg/L acetamide, 58 mg/L allyl alcohol, 1 mg/L acrylonitrile, 222 mg/L cis-and trans-crotononitrile, and 2850 mg/L methacrylonitrile. The UV spectrum of the starting material in a 1 cm path length cell showed absorbances of 0.0521 at 254 nm, 0.7724 at 220 nm, 2.3421 at 207 nm, 2.1751 at 200 nm, and 1.1966 at 190 nm. A conditioned bed of 10.1 g of dry Amberlyst 15 ion exchange resin, H+ form, bed diameter 1.2 cm, bed length 20 cm, was prepared. 80 mL of acetonitrile was passed through the resin by downward flow at 80 mL/hr at room temperature. The UV spectrum of the eluent in a 1 cm path length cell showed absorbances of 0.0041 at 254 nm, 0.1641 at 220 nm, 1.6003 at 207 nm, 2.0561 at 200 nm, and 1.1977 at 190 nm. The eluent contained no detectable oxazole, 5.9 mg/L acetamide, 58 mg/L allyl alcohol, 1 mg/L acrylonitrile, 230 mg/L cis- and trans-crotononitrile, and 2880 mg/L methacrylonitrile.

EXAMPLE 3

Acetonitrile was recovered from crude acetonitrile in a continuous recovery unit at light ends column reflux ratio 3.58:1, drying column reflux ratio 3.48:1, and product column reflux ratio 6.49:1. The recovered acetonitrile contained 11.6 mg/L acetamide and 0.6 mg/L acrylonitrile. Allyl alcohol, cis- and trans-crotononitrile, methacrylonitrile, oxazole, and pyridine were below detection limits. The UV spectrum of this material in a 1 cm path length cell showed absorbances of 0.016 at 254 nm, 0.085 at 220 nm, and 3.481 at 190 nm. A resin bed was prepared from 10.1 g (20 cc) of fresh, dry Amberlyst 15 ion exchange resin, H+ form, bed diameter 1.2 cm, bed length 20 cm. After the bed was flushed with 200 mL of acetonitrile at 160 mL/hr, 100 mL of acetonitrile was passed through the resin by downward flow at 80 mL/hr at room temperature. The UV spectrum in a 1 cm path length cell of a sample taken from the last 25 mL of eluent showed absorbances of 0.012 at 254 nm, 0.054 at 220 nm, and 1.022 at 190 nm. The concentration of acetamide in the eluent was less than 0.3 mg/L.

EXAMPLE 4

Acetonitrile was recovered from crude acetonitrile in a continuous recovery unit at light ends column reflux ratio 4.78:1, drying column reflux ratio 4.61:1, and product column reflux ratio 8.38:1. The recovered acetonitrile contained 12.7 mg/L acetamide and <0.1 mg/L acrylonitrile. Allyl alcohol, cis- and trans-crotononitrile, methacrylonitrile, oxazole, and pyridine were below detection limits. The UV spectrum of this material in a 1 cm path length cell showed absorbances of 0.008 at 254 nm, 0.060 at 220 nm, and 2.422 at 190 nm. A resin bed was prepared from 10.1 g (20 cc) of fresh, dry Amberlyst 15 ion exchange resin, H+ form, bed diameter 1.2 cm, bed length 20 cm. After the bed was flushed with 200 mL of acetonitrile at 160 mL/hr, 100 mL of acetonitrile was passed through the resin by downward flow at 80 mL/hr. The UV spectrum in a 1 cm path length cell of a sample taken from the last 25 mL of eluent showed absorbances of 0.012 at 254 nm, 0.041 at 220 nm, and 0.792 at 190 nm. The concentration of acetamide in the eluent was less than 0.3 mg/L.

EXAMPLE 5

Acetonitrile was recovered from crude acetonitrile in a continuous recovery unit at light ends column reflux ratio 6.08:1, drying column reflux ratio 5.27:1, and product column reflux ratio 13.14:1. The recovered acetonitrile contained 20.3 mg/L acetamide and <0.1 mg/L acrylonitrile. Allyl alcohol, cis- and trans-crotononitrile, methacrylonitrile, oxazole, and pyridine were below detection limits. The UV spectrum of this material in a 1 cm path length cell showed absorbances of 0.000 at 254 nm, 0.052 at 220 nm, and 2.979 at 190 nm. A resin bed was prepared from 10.1 g (20 cc) of fresh, dry Amberlyst 15 ion exchange resin, H+ form, bed diameter 1.2 cm, bed length 20 cm. After the bed was flushed with 200 mL of acetonitrile at 160 mL/hr, 100 mL of acetonitrile was passed through the resin by downward flow at 80 mL/hr at room temperature. The UV spectrum in a 1 cm path length cell of a sample taken from the last 25 mL of eluent showed absorbances of 0.003 at 254 nm, 0.037 at 220 nm, and 0.625 at 190 nm. The concentration of acetamide in the eluent was less than 0.3 mg/L.

EXAMPLE 6

Acetonitrile was recovered from crude in a continuous recovery unit at light ends column reflux ratio between 5.08:1 and 5.70:1, drying column reflux ratio between 4.86:1 and 4.97:1, and product column reflux ratio between 9.77:1 and 12.12:1. The recovered acetonitrile contained approximately 16 mg/L acetamide and <0.1 mg/L acrylonitrile. Allyl alcohol, cis- and trans-crotononitrile, methacrylonitrile, oxazole, and pyridine were below detection limits. The UV spectrum of this material in a 1 cm path length cell showed absorbances of 0.005 at 254 nm, 0.036 at 220 nm, and 3.32 at 190 nm. A resin bed was prepared from 10.1 g (20 cc) of fresh, dry Amberlyst 15 ion exchange resin, H+ form, bed diameter 1.2 cm, bed length 20 cm. After the bed was flushed with 200 mL of acetonitrile at 160 mL/hr, 1000 mL of acetonitrile was passed through the resin by downward flow at 80 mL/hr at room temperature. The UV spectrum of the eluent in a 1 cm path length cell showed absorbances of 0.0034 at 254 nm, 0.0401 at 220 nm, and 0.5634 at 190 nm. The concentration of acetamide in the eluent was less than 0.3 mg/L.

400.1 g of the Amberlyst 15-treated material was then placed in a 1 L three neck flask affixed with a 30 cm×1 cm i.d. glass vacuum jacketed fractionating column, unpacked, and a coldfinger distillation head. The ground glass joints were sealed with Teflon tape. The first 16.7 g of distillate was discarded, and the remaining distillate was collected together and filtered through a 0.2μ Nylon filter disk. The last fraction, 40.35 g, and the pot residue, 17.58 g, were discarded. The UV spectrum of the collected distillate in a 1 cm path length cell showed absorbances of 0.0008 at 254 nm, 0.0205 at 220 nm, and 0.5072 at 190 nm.

EXAMPLE 7

Acetonitrile was recovered from crude acetonitrile in a continuous recovery unit at light ends column reflux ratio 4.53:1, drying column reflux ratio 5.24:1, and product column reflux ratio 10.39:1. The recovered acetonitrile contained 12.6 mg/L acetamide and appx. 0.05 mg/L acrylonitrile. Allyl alcohol, cis- and trans-crotononitrile, methacrylonitrile, oxazole, and pyridine were below detection limits. The UV spectrum of this material in a 1 cm path length cell showed absorbances of 0.0043 at 254 nm, 0.0401 at 220 nm, and 1.2350 at 190 nm. A resin bed was prepared from 4.0 g (8 cc) of fresh, dry Amberlyst 15 ion exchange resin, H+ form, bed diameter 0.8 cm, bed length 18 cm. The bed was conditioned at room temperature by upward flow with water at 96 mL/hr for 90 minutes, followed by 10%

(w/w) H$_2$SO$_4$ (aq) at 38 mL/hr for 70 minutes, then water at 38 mL/hr for 60 minutes, then water at 99 mL/hr for 75 minutes, then purified acetonitrile at 33 mL/hr for 18 hours. Then 3700 mL of recovered acetonitrile was passed through the resin by upward flow at rates from 32.7 mL/hr to 106.3 mL/hr at room temperature. The UV spectra of samples taken during the experiment showed no significant changes with time or with flow rate. The UV spectrum of the combined eluent in a 1 cm path length cell showed absorbances of 0.0020 at 254 nm, 0.0167 at 220 nm, and 0.4169 at 190 nm. No detectable acetamide was found in the eluent.

EXAMPLE 8

Acetonitrile was recovered from crude acetonitrile in a continuous recovery unit at light ends column reflux ratio 4.53:1, drying column reflux ratio 5.24:1, and product column reflux ratio 10.39:1. The recovered acetonitrile contained 12.6 mg/L acetamide and appx. 0.05 mg/L acrylonitrile. Allyl alcohol, cis- and trans-crotononitrile, methacrylonitrile, oxazole, and pyridine were below detection limits. The UV spectrum of this material in a 1 cm path length cell showed absorbances of 0.0043 at 254 nm, 0.0401 at 220 nm, and 1.2350 at 190 nm. A resin bed was prepared from 1.25 g of fresh, dry Dowex 50W-X8 ion exchange resin, H+ form, bed diameter 0.8 cm, bed length 4 cm. The bed was conditioned at room temperature by upward flow with water at 1.14 mL/min for 81 minutes, followed by 10% (w/w) H$_2$SO$_4$ (aq) at 0.124 mL/min for 84 minutes, then water at 0.124 mL/min for 30 minutes, then water at 0.37 mL/hr for 73 minutes, then purified acetonitrile at 33.2 mL/hr for 17.25 hours. Then recovered acetonitrile was passed through the resin by upward flow at 33.2 mL/hr over a 102 hour period at room temperature. The UV spectra of samples taken during the experiment showed no significant changes with time or with flow rate. The UV spectrum of the combined eluent in a 1 cm path length cell after 102 hours showed absorbances of 0.0013 at 254 nm, 0.0120 at 220 nm, and 0.3896 at 190 nm.

EXAMPLE 9

Acetonitrile was recovered from crude acetonitrile in a continuous recovery unit at light ends column reflux ratio 4.53:1, drying column reflux ratio 5.24:1, and product column reflux ratio 10.39:1. The recovered acetonitrile contained 12.6 mg/L acetamide and appx. 0.05 mg/L acrylonitrile. Allyl alcohol, cis- and trans-crotononitrile, methacrylonitrile, oxazole, and pyridine were below detection limits. The UV spectrum of this material in a 1 cm path length cell showed absorbances of 0.0043 at 254 nm, 0.0401 at 220 nm, and 1.2350 at 190 nm. A resin bed was prepared from 4.0 g of fresh, dry Amberlyst 15 ion exchange resin, H+ form, bed diameter 0.8 cm, bed length 18 cm. The bed was conditioned at room temperature by upward flow with water at 96 mL/hr for 60 minutes, followed by 10% (w/w) H$_2$SO$_4$ (aq) at 26.8 mL/hr for 60 minutes, then water at 26.8 mL/hr for 38 minutes, then water at 96 mL/hr for 60 minutes, then purified acetonitrile at 33.2 mL/hr for 26 hours. Then recovered acetonitrile was passed through the resin by upward flow at flow rates ranging from 33.2 mL/hr to 225 mL/hr until a total of 20 L of resin-treated material was collected. The UV spectra of samples taken during the experiment showed no significant changes with time or with flow rate. The UV spectrum of the combined eluent in a 1 cm path length cell showed absorbances of 0.0013 at 254 nm, 0.0167 at 220 nm, and 0.3973 at 190 nm. Analyses of the combined eluent showed an assay of 99.97% acetonitrile; APHA color <5; 0.315 µeq/g titratable acid; 0.0019 µeq/g titratable base; 0.026% water; 0.01 ppm acrylonitrile; 49 ppm propionitrile; and acetone, allyl alcohol, cis- and trans-crotononitrile, methacrylonitrile, oxazole, and pyridine were all below detection limits.

EXAMPLE 10

Acetonitrile was recovered from crude acetonitrile in a continuous recovery unit at light ends column reflux ratio 4.53:1, drying column reflux ratio 5.24:1, and product column reflux ratio 10.39:1. The recovered acetonitrile contained 12.6 mg/L acetamide and appx. 0.05 mg/L acrylonitrile. Allyl alcohol, cis- and trans-crotononitrile, methacrylonitrile, oxazole, and pyridine were below detection limits. The UV spectrum of this material in a 1 cm path length cell showed absorbances of 0.0043 at 254 nm, 0.0401 at 220 nm, and 1.2350 at 190 nm. A resin bed was prepared from 1.25 g of fresh, dry Amberlite IRC-50 ion exchange resin, H+ form, bed diameter 0.8 cm, bed length 4 cm. The bed was conditioned at room temperature by upward flow with water at 1.14 mL/min for 25 minutes, followed by 10% (w/w) H$_2$SO$_4$ (aq) at 0.124 mL/min for 80 minutes, then water at 0.124 mL/min for 30 minutes, then water at 0.37 mL/hr for 60 minutes, then purified acetonitrile at 37 mL/hr for 18 hours. Then recovered acetonitrile was passed through the resin by upward flow at 37 mL/hr over a 2 hour period at room temperature. The UV spectra of samples taken during the first two hours of elution showed no significant changes with time. The UV spectrum of the combined eluent in a 1 cm path length cell after 102 hours showed absorbances of 0.0024 at 254 nm, 0.0186 at 220 nm, and 0.3653 at 190 nm. No detectable acetamide was found in the eluent. As acetonitrile eluted through the column further, acetamide began to appear in the eluent.

The above examples and descriptions are not intended to be exhaustive or limiting as to the description of the present invention, but merely as illustrative of the practice of the process of the present invention. It is evident that many alternatives, modifications and variations will be apparent to those skilled in the art in light of the foregoing description. Accordingly, it is intended to embrace all such alternatives, modifications and variations as fall within the spirit and broad scope of the appended claims.

What we claim as our invention is:

1. A process of producing highly purified acetonitrile having no more than about 0.3 milligrams of acetamide per liter of acetonitrile comprising (1) distilling crude acetonitrile in a first distillation column affixed with a first overhead reflux loop at a first pressure of at least 1 atmosphere to remove HCN, producing a first acetonitrile/water azeotrope and a first bottom product containing water, (2) distilling the first azeotrope in a second distillation column affixed with a second overhead reflux loop at a second pressure less than 1 atmosphere to separate the first azeotrope into a second bottoms product containing water and a second acetonitrile/water azeotrope having a greater acetonitrile concentration than that the first azeotrope, (3) distilling the second acetonitrile/water azeotrope in a third distillation column affixed with a third overhead reflux loop at a third pressure above 1 atmosphere to produce a third acetonitrile/water azeotrope containing substantially all of the water from the second azeotrope, a third bottoms product comprising acetonitrile and heavy organics and a side stream comprising highly pure acetonitrile, and (4) passing the highly pure acetonitrile side stream through an acidic ion exchange resin to further purify said highly pure acetonitrile producing highly purified acetonitrile having a UV cutoff for impurities of <190 nm wherein the reflux ratios in Steps 1, 2 and 3 are kept at greater than 3 to 1, greater than 3.4 to 1 and greater than 6.4 to 1, respectively.

2. The process of claim 1 wherein the reflux ratio in step 1 is greater than about 4.4:1.

3. The process of claim 2 wherein the reflux ratio in step 2 is greater than about 4.5:1.

4. The process of claim 3 wherein the reflux ratio in step 3 is greater than about 8:1.

5. The process of claim 1 wherein the acidic ion exchange resin is selected to include a strong acid incorporating sulfonic acid functional groups.

6. The process of claim 1 wherein the acidic ion exchange resin is selected to include weak acid resin incorporating carboxylic acid functional groups.

7. The process of claim 1 further comprising distilling the purified acetonitrile recovered from the acidic ion exchange resin.

8. The process of claim 7 wherein the reflux ratio in step 1 is greater than about 4.4:1.

9. The process of claim 8 wherein the reflux ratio in step 2 is greater than about 4.5:1.

10. The process of claim 9 wherein the reflux ratio in step 3 is greater than about 8:1.

11. The process of claim 7 wherein the acidic ion exchange resin is selected to include a strong acid incorporating sulfonic acid functional groups.

12. The process of claim 7 wherein the acidic ion exchange resin is selected to include weak acid resin incorporating carboxylic acid function groups.

13. A process of producing highly purified acetonitrile comprising:
   distilling crude acetonitrile in a first distillation column affixed with a first overhead reflux loop operating at a reflux ratio of greater than 3 to 1 and at a first pressure of at least 1 atmosphere for removing HCN to produce a first acetonitrile/water azeotrope and a first bottom product containing water;
   distilling the first azeotrope in a second distillation column affixed with a second overhead reflux loop operating at a reflux ratio of greater than 3.4 to 1 and at a second pressure less than 1 atmosphere to separate the first azeotrope into a second bottoms product containing water and a second acetonitrile/water azeotrope having a greater acetonitrile concentration than that of the first azeotrope;
   distilling the second acetonitrile/water azeotrope in a third distillation column affixed with a third overhead reflux loop operating at a reflux ratio of greater than 6.4 to 1 and at a third pressure above 1 atmosphere to produce a third acetonitrile/water azeotrope containing substantially all of the water from the second azeotrope, a third bottoms product comprising acetonitrile and heavy organics, and a side stream comprising highly pure acetonitrile; and
   passing the highly pure acetonitrile side stream through an acidic ion exchange resin to further purify the highly pure acetonitrile producing highly purified acetonitrile having an assay of at least 99.97% acetonitrile.

14. The process of claim 13 wherein the reflux ratio of the first overhead reflux loop is greater than about 4.4:1; the reflux ratio in the second overhead reflux loop is greater than about 4.5:1; and the reflux ratio in the third overhead reflux loop is greater than about 8:1.

15. The process of claim 13 wherein the acidic ion exchange resin is selected to include a strong acid incorporating sulfonic acid functional groups.

16. The process of claim 13 wherein the acidic ion exchange resin is selected to include weak acid resin incorporating carboxylic acid functional groups.

17. The process of claim 13 further comprising distilling the purified acetonitrile recovered from the acidic ion exchange resin.

* * * * *